United States Patent
Schwab

(10) Patent No.: US 8,118,841 B2
(45) Date of Patent: Feb. 21, 2012

(54) DEVICE FOR DYNAMIC SPINAL FIXATION FOR CORRECTION OF SPINAL DEFORMITIES

(75) Inventor: Frank J. Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 11/084,241

(22) Filed: Mar. 21, 2005

(65) Prior Publication Data

US 2005/0216004 A1   Sep. 29, 2005

Related U.S. Application Data

(60) Provisional application No. 60/555,440, filed on Mar. 23, 2004.

(51) Int. Cl.
*A61B 17/70* (2006.01)
(52) U.S. Cl. .......................... 606/263; 606/254; 606/257
(58) Field of Classification Search .................. 606/61, 606/246–279
See application file for complete search history.

(56) References Cited

U.S. PATENT DOCUMENTS

| | | | | |
|---|---|---|---|---|
| 4,041,939 A | * | 8/1977 | Hall | 606/61 |
| 4,047,524 A | | 9/1977 | Hall | |
| 4,641,636 A | | 2/1987 | Cotrel | |
| 4,697,582 A | * | 10/1987 | William | 606/61 |
| 4,815,453 A | * | 3/1989 | Cotrel | 606/61 |
| 4,887,595 A | * | 12/1989 | Heinig et al. | 606/61 |
| 5,067,955 A | * | 11/1991 | Cotrel | 606/61 |
| 5,092,866 A | | 3/1992 | Breard et al. | |
| 5,102,412 A | | 4/1992 | Rogozinski | |
| 5,180,393 A | * | 1/1993 | Commarmond | 623/13.14 |
| 5,181,917 A | | 1/1993 | Rogozinski | |
| 5,281,223 A | | 1/1994 | Ray | |
| 5,385,565 A | | 1/1995 | Ray | |
| 5,387,213 A | * | 2/1995 | Breard et al. | 606/61 |
| 5,415,661 A | * | 5/1995 | Holmes | 606/69 |
| 5,603,714 A | * | 2/1997 | Kaneda et al. | 606/61 |
| 5,702,395 A | | 12/1997 | Hopf | |
| 5,704,936 A | * | 1/1998 | Mazel | 606/61 |
| 5,879,351 A | * | 3/1999 | Viart | 606/61 |
| RE36,221 E | | 6/1999 | Breard et al. | |
| 6,074,393 A | * | 6/2000 | Sitoto | 606/73 |

(Continued)

FOREIGN PATENT DOCUMENTS

FR     2689750 A1     10/1993

(Continued)

OTHER PUBLICATIONS

Supplementary European Search Report for European Application No. PCT/US2005009251 (The European counterpart of the parent application) mailed Dec. 19, 2008.

*Primary Examiner* — Eduardo C Robert
*Assistant Examiner* — Mary Hoffman

(57) ABSTRACT

Embodiments described herein relate to a method and system for dynamic spinal fixation for the correction of spinal deformities, and more specifically pertains to a method and system permitting a correction of spinal deformity without rigid fixation of the vertebral bodies. The embodiments are useful in correcting spinal deformities, including all types of scoliosis or other misalignments affecting the vertebral column. The positioning of devices and elements permits a gradual correction of a three dimensional spinal deformity through operative intervention and/or the natural growth of the vertebrae and spinal column.

18 Claims, 12 Drawing Sheets

U.S. PATENT DOCUMENTS

| | | | |
|---|---|---|---|
| 6,248,106 B1 | 6/2001 | Ferree | |
| 6,296,643 B1 | 10/2001 | Hopf et al. | |
| 6,299,613 B1 | 10/2001 | Ogilvie et al. | |
| 6,436,099 B1 | 8/2002 | Drewry et al. | |
| 6,468,309 B1 | 10/2002 | Lieberman | |
| 6,551,320 B2 | 4/2003 | Lieberman | |
| 6,616,669 B2 | 9/2003 | Ogilvie et al. | |
| 6,652,585 B2 | 11/2003 | Lange | |
| 6,746,450 B1 | 6/2004 | Wall et al. | |
| 6,966,910 B2 * | 11/2005 | Ritland | 606/61 |
| 6,989,011 B2 * | 1/2006 | Paul et al. | 606/61 |
| 2002/0055740 A1 | 5/2002 | Lieberman | |
| 2002/0143329 A1 * | 10/2002 | Serhan et al. | 606/61 |
| 2003/0220643 A1 * | 11/2003 | Ferree | 606/61 |
| 2005/0203511 A1 * | 9/2005 | Wilson-MacDonald et al. | 606/61 |

FOREIGN PATENT DOCUMENTS

| | | | |
|---|---|---|---|
| FR | 2697428 | * | 5/1994 |
| GB | 2382304 A | | 5/2003 |
| WO | 0064360 A2 | | 11/2000 |

* cited by examiner

DEVICE FOR DYNAMIC SPINAL FIXATION FOR CORRECTION OF SPINAL DEFORMITIES

This application claims priority to provisional patent application entitled "Ensemble of Devices for Dynamic Connection of a System for Spinal Fixation and a System of Fixation Containing Such Elements for Correction of Spinal Deformity," filed Mar. 23, 2004, Ser. No. 60/555,440, the disclosure of which is incorporated by reference herein in its entirety.

FIELD OF THE INVENTION

Embodiments of the invention relate to a system and method for dynamic spinal fixation for the correction of spinal deformities, and more specifically pertains to a system and method permitting a correction of spinal deformity without rigid fixation of the vertebral bodies. The embodiments are useful in correcting spinal deformities, including all types of scoliosis or other misalignments affecting the vertebral column.

DESCRIPTION OF RELATED ART

There are numerous types of instrumentation that provide a connection between vertebral levels with the purpose of obtaining correction of a deformity. These instrumentations typically consist of various types of anchorage to bone (cables, hooks, screws) connected together by a rod-based system. It is possible to correct some deformities with these systems, based in part on the surgeon's ability to adequately contour the rod. The rigidity imparted by the rod reduces mobility of the spinal column and thereby permits the creation of an arthrodesis (spinal fusion between vertebrae).

The latter systems of spinal instrumentation pose the inconvenience of definitively immobilizing the spinal column thereby limiting any further growth of the affected portions of the spine in a child with spinal deformity. An additional concern (particularly in skeletally mature individuals) brought by these instrumentation systems relates to the markedly elevated forces seen at the ends of a rigid construct. This can lead to accelerated degeneration and failure of spinal elements (intervertebral discs, facet joints, ligaments).

A further concern and limitation of these instrumentation systems relates to the mechanism of deformity correction that principally addresses the sagittal and frontal plane but only minimally (if at all) addresses vertebral rotation. The latter rotation refers to the horizontal plane of a vertebra in the upright spine. While in a normal spinal column the posterior elements of the vertebra are symmetrically aligned in a posterior view, a vertebra with axial rotation as seen in scoliosis has a marked deviation of posterior elements into the concavity of the curvature. With current instrumentation systems, failure to address the axial rotation of the spine can leave a marked residual deformity (particularly at the apex of a scoliotic curvature) and rib cage asymmetry. An additional concern related to these instrumentation systems relates to the invasive nature of their surgical placement, which carries significant morbidity.

The art has proposed various techniques to address some of the aforementioned concerns. For example, U.S. Pat. No. 5,092,866 (and its Reissue patent Re 36,221) discloses a flexible inter-vertebral stabilizer having one or more flexible ligaments. The flexible ligaments typically are attached to vertebral fixation elements, such as screws. The constraining force (or tension) of the flexible ligament is said to make it possible to compensate for defects or deformations of the spinal column by permitting sufficient clearance between the vertebrae not to hinder the patient in the flexional or torsional movements of his trunk.

U.S. Pat. Nos. 5,281,223 and 5,385,565 disclose a tool and method for derotating a scoliotic spine while it is being manipulated from a scoliotic configuration to a kyphotic configuration. The tool applies a de-rotating force to the affected vertebral bodies to bring them into conformity, and then fixes the spine using rigid fixation instrumentation systems such as rods, and the like.

U.S. Pat. No. 6,551,320 discloses an apparatus and method for correcting spinal deformity by placing certain anchors in the vertebral bodies, inserting a cable through passages in the anchors, tightening the cable to bring the misaligned vertebrae into alignment, and then fixing the spine by tightening the inflexible cable.

Recent advances attempt to correct spinal deformities through a fusionless process whereby the vertebral bodies are not fused, or fixed, relative to one another. U.S. Pat. Nos. 6,296,643, 6,299,613, and 6,436,099, all disclose various techniques for fusionless treatment of spinal deformities. These documents disclose in general fixation elements (or blocks) attached to vertebral bodies, and tethers attached to the fixation elements, or blocks.

The description herein of disadvantages, concerns, and/or problems associated with known devices, apparatus, systems, and methods is not intended to limit the scope of the embodiments described herein to their exclusion. Indeed, various aspects of the embodiments may include one or more of the known devices, apparatus, systems, and methods, without suffering from the described disadvantages, concerns, and/or problems.

SUMMARY

There is need to provide a fusionless treatment for spinal deformities that is relatively simple and easy to implement. There also is a need to provide a fusionless ability to de-rotate an improperly rotated and improperly aligned vertebral body, without having to permanently fix the vertebral bodies with respect to one another. There also is a need to provide a treatment for spinal deformities in skeletally immature individuals that allows the natural growth of the spine to correct the deformity.

Features of embodiments of the invention satisfy these needs by providing improvements and solutions for treatment of spinal deformities, such as idiopathic scoliosis, including forms affecting skeletally immature individuals with remaining growth potential. The embodiments, through a non-linear placement of vertebral anchor means and/or flexible interconnection, together with the use of a flexible interconnection, permits the correction of spine deformity either during operative intervention, or in a progressive manner with continued spinal growth in a skeletally immature individual. Embodiments of the invention also enable the correction through a minimally invasive surgical approach.

In accordance with these and other features of the embodiments, there is provided a system for treating a spinal deformity in a skeletally mature or immature spine comprising at least three vertebral anchor means for anchoring into three different vertebral bodies, respectively, the vertebral anchor means optionally being positionable in the vertebral bodies in a non-linear manner. The system further includes at least one flexible interconnection means for attaching to the vertebral anchor means in a non-linear manner. In accordance with the embodiment, for skeletally immature spines, the flexible interconnection means constrains spinal growth in at least one direction thereby creating tension on the vertebral anchor means and flexible interconnection means, causing the resulting flexible interconnection means to be less non-linear after spinal growth than the flexible interconnection means prior to spinal growth. It should be noted that correction of deformity can be achieved at the time of surgery through tensioning of the flexible interconnecting means for skeletally mature of immature patients, and then securing the flexible interconnecting means. Due to the flexible nature of the flexible interconnecting means, mobility is not as adversely affected, when compared to rigid cable fixation systems known in the art.

In accordance with other features of embodiments described herein, there is provided a method of treating a spinal deformity in a skeletally immature spine comprising positioning at least three anchors in at least three different vertebral bodies. The anchors are optionally positioned in such a manner that they are not vertically aligned. The method further includes attaching a flexible interconnection to the at least three anchors such that the flexible interconnection is non-linear. In accordance with this embodiment, the flexible interconnection constrains spinal growth in at least one direction thereby creating tension on the vertebral anchor means and/or the flexible interconnection means and causing the resulting flexible interconnection means to be less non-linear after spinal growth than the flexible interconnection means prior to spinal growth. In another embodiment, as is the case with a skeletally mature spine, the method further includes tensioning the flexible interconnection means to be less non-linear after tensioning than prior to tensioning, and securing the flexible interconnection means to at least one of the anchors.

These and other features of embodiments will be readily apparent from the detailed description that follows.

DETAILED DESCRIPTION

Figure 1:
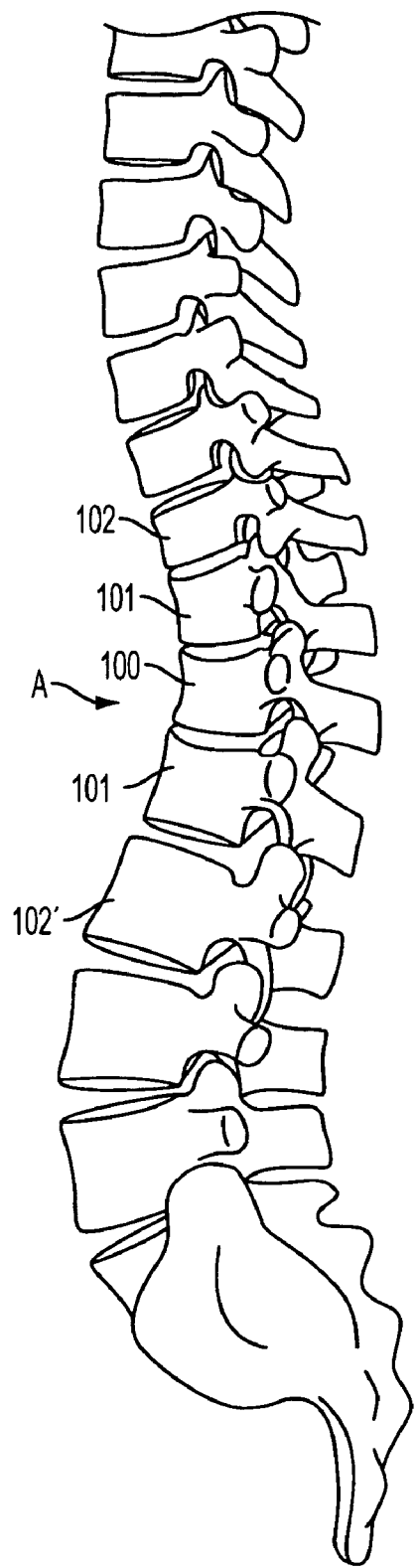
FIG. 1 illustrates a sagittal view of a spine with deformity (scoliosis)

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a vertebral anchor" includes a plurality of such anchors, as well as a single anchor, and a reference to "a flexible interconnection" is a reference to one or more flexible interconnections and equivalents thereof known to those skilled in the art, and so forth.

Throughout this description, the term "non-linear" insofar as it relates to the placement of anchor means in vertebral bodies denotes that the anchor means are anchored in adjacent vertebral bodies non-linearly and/or that the connection to the flexible interconnecting element is non-linear. That is, non-linear would denote the inability to draw a straight line between three anchor means in three adjacent vertebral bodies. Non-linear also would denote anchor means positioned in different areas on adjacent vertebral bodies—one closer to a posterior portion and another closer to an anterior portion of an adjacent vertebral body. An embodiment described herein relates to the use of anchoring means that comprise more than one anchor. In this embodiment, the anchoring means may be linear, but the flexible interconnection means is attached to anchoring means that are non-linear (e.g., attaching the flexible interconnection means to alternating anchoring means from one vertebral body to the next).

Embodiments of the invention provide a system for treating a spinal deformity in a skeletally mature or immature spine comprising at least three vertebral anchor means for anchoring into three different vertebral bodies, respectively, the vertebral anchor means optionally being positionable in the vertebral bodies in a non-linear manner. The system further includes at least one flexible interconnection means for attaching to the vertebral anchor means in a non-linear manner. In accordance with the embodiment, the flexible interconnection means constrains spinal growth (in the immature spine) in at least one direction thereby creating tension on the flexible interconnection means, causing the resulting flexible interconnection means to be less non-linear than the flexible interconnection means prior to spinal growth. In the setting of a skeletally mature spine the intraoperative tensioning of the flexible interconnecting means can afford altered intervertebral alignment of the spinal column.

An additional embodiment of the invention provides a method of treating a spinal deformity in a skeletally immature spine comprising positioning at least three anchors in at least three different vertebral bodies such that the anchors are not vertically aligned. The method further includes attaching a flexible interconnection to the at least three anchors such that the flexible interconnection is non-linear. In accordance with this embodiment, the flexible interconnection constrains spinal growth in at least one direction thereby creating tension on the flexible interconnection means and causing the resulting flexible interconnection means to be less non-linear than the flexible interconnection means prior to spinal growth. For a skeletally mature spine, intraoperative tensioning of the flexible interconnecting means can afford altered intervertebral alignment of the spinal column.

The embodiments described herein preferably relate to a system of at least 3 vertebral bone anchoring means, implanted in a non-linear fashion, and connected to one another by a flexible interconnection means. It is preferred that the flexible interconnection means include a biocompatible ligament, or a tether such as, or similar to those disclosed in U.S. Pat. Nos. 5,092,866, 6,296,643, 6,299,613, 6,551,320, and 6,436,099, the disclosures of which are incorporated by reference herein in their entirety.

It is preferred in the embodiments to implant the anchoring means on the convexity of the spinal deformity, which is to be corrected. In its primary, or simplest embodiment, one anchoring means is implanted per vertebra across at least 3 vertebrae connected to one another by flexible interconnection means. In one embodiment, the anchoring means at the ends of the system or construct preferably are implanted in an identical fashion to the desired vertebrae. In this embodiment, the intermediate anchoring means preferably is implanted with an inherent offset with respect to the anchoring means at the ends of the construct. Accordingly, the anchoring means are non-linear in this embodiment.

In accordance with a preferred embodiment, the flexible interconnection means is attached or otherwise secured to at least two of the anchoring means implanted at the ends of the system or construct. While not intending on being bound by any theory of operation, the inventor believes that in this embodiment, the natural growth of the spinal column will tend to increase the distance and cause a distraction between the 2 anchoring means positioned at the ends of the construct. It is believed that the natural distraction occurring between the 2 vertebral fixation points will lead to realignment of the intermediate anchoring means through forces exerted across the flexible interconnection means. When constructed in this manner, the inventor believes that this realignment of the intermediate anchoring means through natural spinal growth will create a rotation of the intermediate vertebra, and consequently, de-rotate an improperly rotated vertebral body.

In a similar manner, intra-operative tensioning of the flexible interconnecting means can permit intervertebral alignment changes in a skeletally mature of immature spine. After tensioning, the flexible interconnecting means can be affixed to one or both of the anchoring means positioned at the ends of the construct. Due to the flexible nature of the flexible interconnecting means, the system still permits sufficient mobility in the patient.

In these embodiments, the system of anchoring means, if positioned on the anterior portion of the vertebrae, are implanted on the convexity of the spinal deformity in order to create a resistance to growth in such a manner that growth will be more significant on the concave side of the deformity. Through a posterior application of anchoring means, the end anchoring means are on the convexity while the intermediate anchoring means is on the concavity of the deformity. The ensemble of vertebral anchoring means and the flexible interconnection means will arrest the progression of evolution of deformity (such as scoliosis) without creating a fusion between the vertebrae of the spine. In this embodiment, the system of anchoring means and the flexible interconnection means permit a three dimensional correction of deformity and scoliosis in growing individuals and children, (or adults, without creating a fusion between vertebrae. It is preferred in this embodiment that the vertebral anchoring means be implanted on the spinal column through the posterior portions of the vertebrae (fixation in the pedicles) or on the anterior aspect of the vertebrae (vertebral body fixation).

In another embodiment, 2 anchoring means are implanted per vertebra across at least 3 vertebrae of the spinal column. In this embodiment, each anchoring means may be linear with respect to a corresponding anchoring means on an adjacent vertebral body. The individual anchoring means on one vertebra preferably, although not necessarily, are interconnected to one another through an additional device resembling a type of plate or staple, which is believed to provide excellent bone anchorage. In this embodiment, only one anchoring means per vertebra is connected to the flexible interconnection means between vertebral levels, and the flexible interconnection means is connected to the anchoring means in a non-linear manner.

In this embodiment, the anchoring means are implanted in similar fashion across the selected vertebral levels. Preferably, if a plate or staple-type device is utilized, the anchoring means are interchangeable on the plate or staple-type device to provide variability with the attachment to the flexible interconnection means connection between vertebrae. The positioning of anchoring means is determined by the inherent geometry of the e device used to connect each anchoring means on each vertebral body.

In an additional embodiment, two anchoring means are implanted on each vertebra, linked to one another through a staple-type device. In this embodiment, at least two anchoring means on one vertebra each contain an attachment to the flexible interconnection means between vertebral levels. The latter permits a correction of deformity across more than three vertebrae and distribution of corrective forces across more than three vertebrae thereby reducing a concentration of forces at the ends of the implanted construct. In this embodiment, the mechanical characteristics, and particularly the effect of spinal growth (in the case of skeletal immaturity) and correction of spinal deformity will be different from the other configurations.

Those skilled in the art will appreciate that the listing of advantages in each embodiment is not repeated for each embodiment, but these advantages remain the same or similar for each respective embodiment. Skilled artisans also will appreciate that the individual elements of the system or construct (e.g., anchoring means, flexible interconnection means, and plate or staple-type devices) may generally be known, but the specific application in the context of spinal deformity and arrangement of elements as well the specific interconnection and positioning of implants is new and inventive.

Any anchoring means can be used in the embodiments described herein that is suitable for providing a sufficient anchor into bone. Suitable anchoring means include bone screws, staples, nails, anchors coated with bone growth promoting substances, screw-anchor combinations, and the like. Preferably, the anchoring means is a bone screw, or a combination of bone screw and bone staple device described in more detail with reference to the figures.

Figure 2:
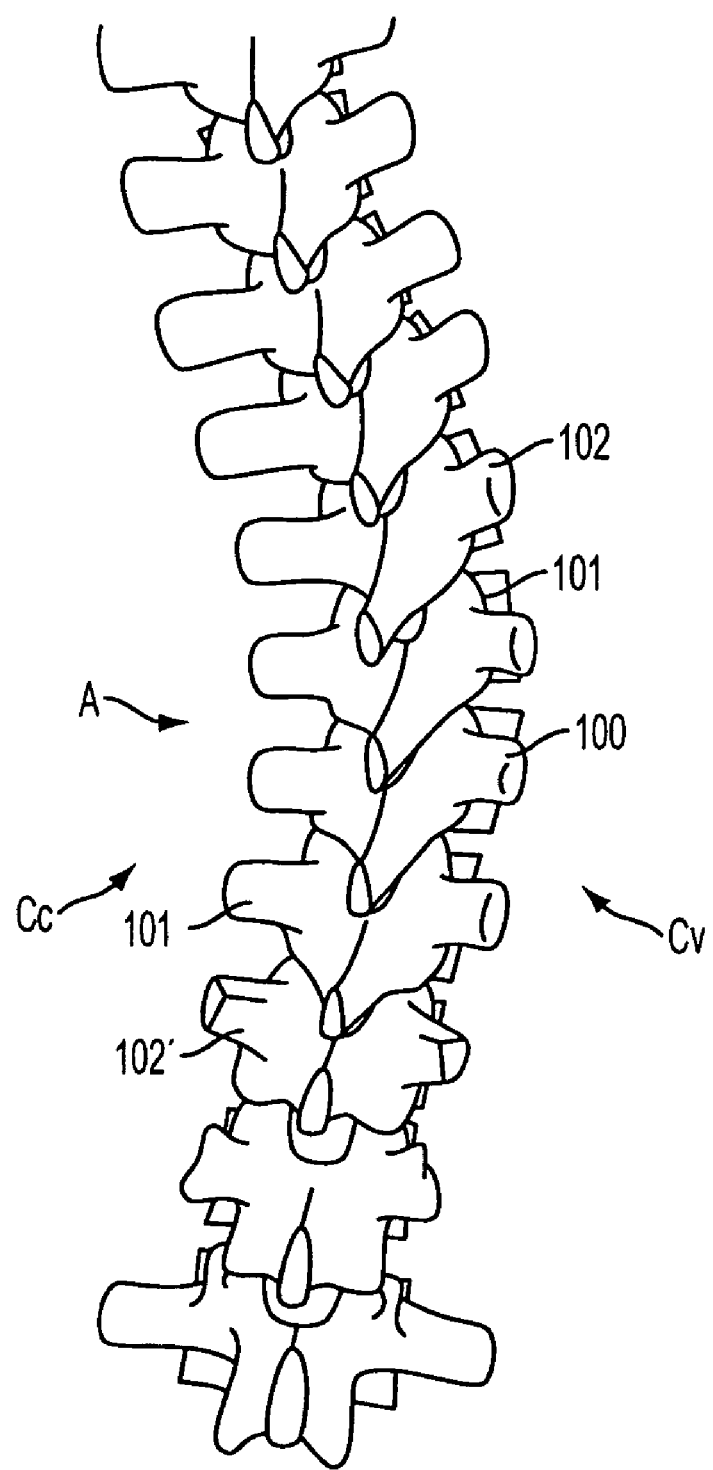
FIG. 2 illustrates a posterior elevated view of a spine with deformity (scoliosis)

FIGS. 1 and 2 illustrate the views of a spine with deformity (scoliosis). The positioning of implants is seen at the convexity aspect of the apex of the deformity (in the figures this is denoted by (A)) across at least 3 vertebrae (100,101,101'). The vertebra (100) situated at the apparent apex of the curvature (A) receives the central anchoring means, whereas vertebral bodies 101 and 101' receive anchoring means and are connected in a non-linear manner with a flexible interconnection means.

Figure 11:
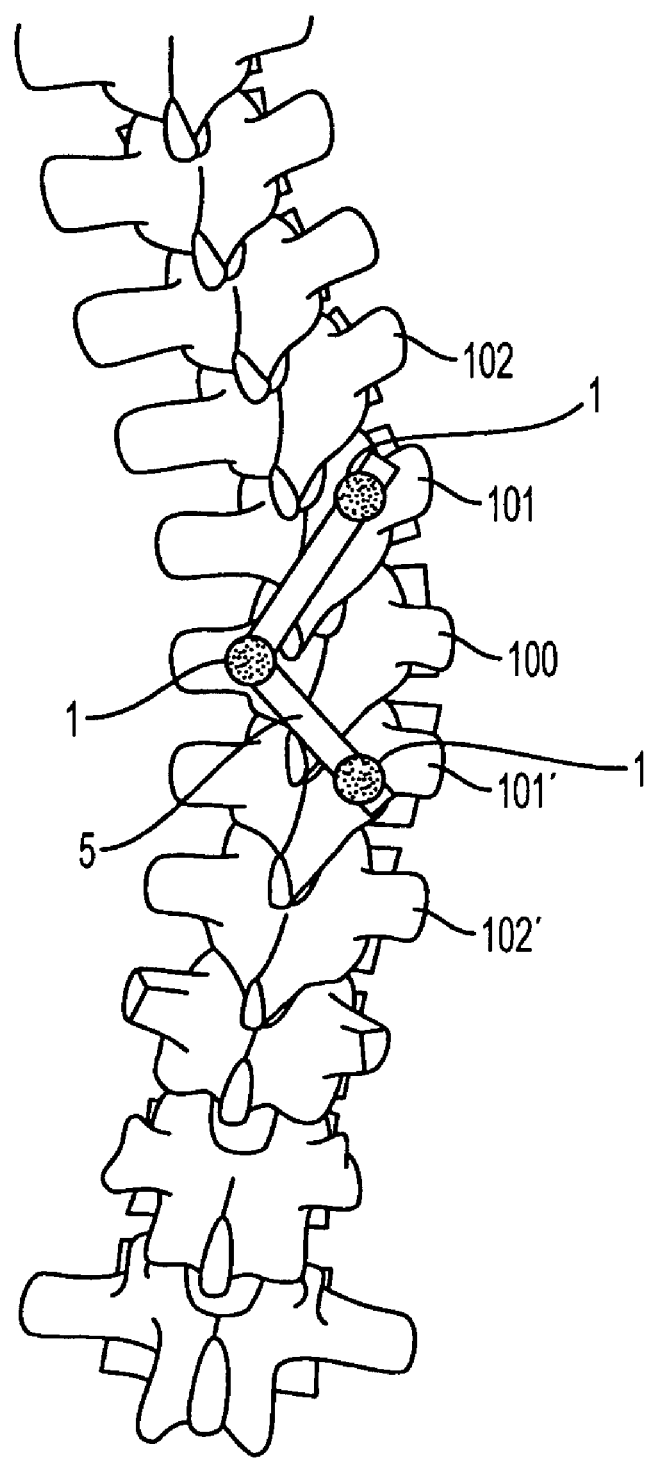
FIG. 11 illustrates an embodiment, but in a posterior application, as depicted in a posterior view of the spine.

FIG. 2 represents a posterior view of a spinal deformity with illustration of the concavity (Cc) and the convexity (Cv) of the deformity (scoliosis). In the configuration of a posterior fixation, that is to say via pedicular fixation (FIG. 11), the bone fixation of the central anchoring means is placed at the concave (Cc) aspect of the deformity. In the configuration of bone fixation on the vertebral body anteriorly (FIGS. 3,4 and 5), the ensemble of anchoring means preferably are positioned on the convex portion (Cv) of the deformity. Using the guidelines provided herein, skilled artisans will be capable of positioning anchoring means in a suitable manner to provide the requisite correction of deformity.

Figure 3:
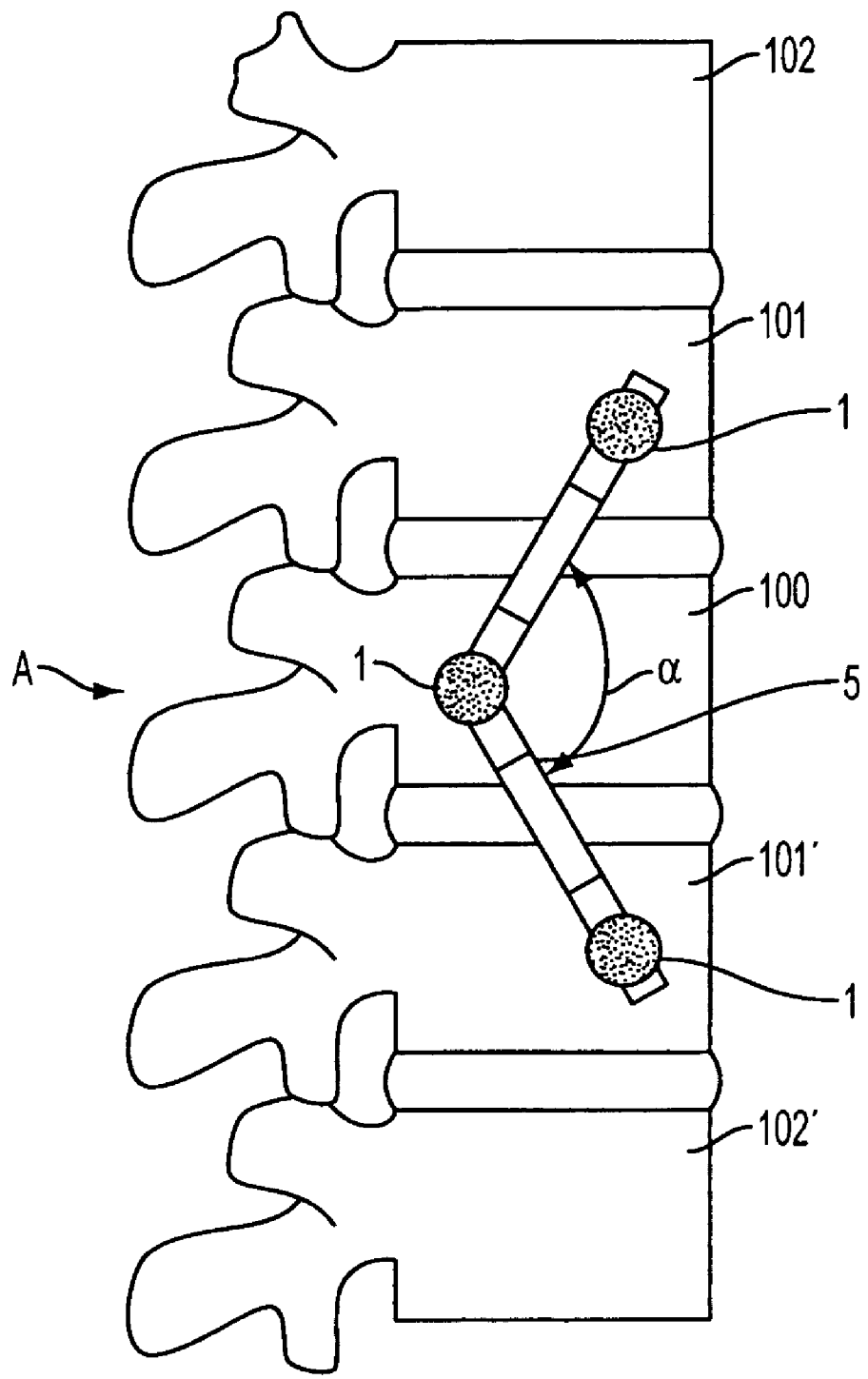
FIG. 3 illustrates an embodiment through an anterior application seen in a sagittal view of the spine.
Figure 12:
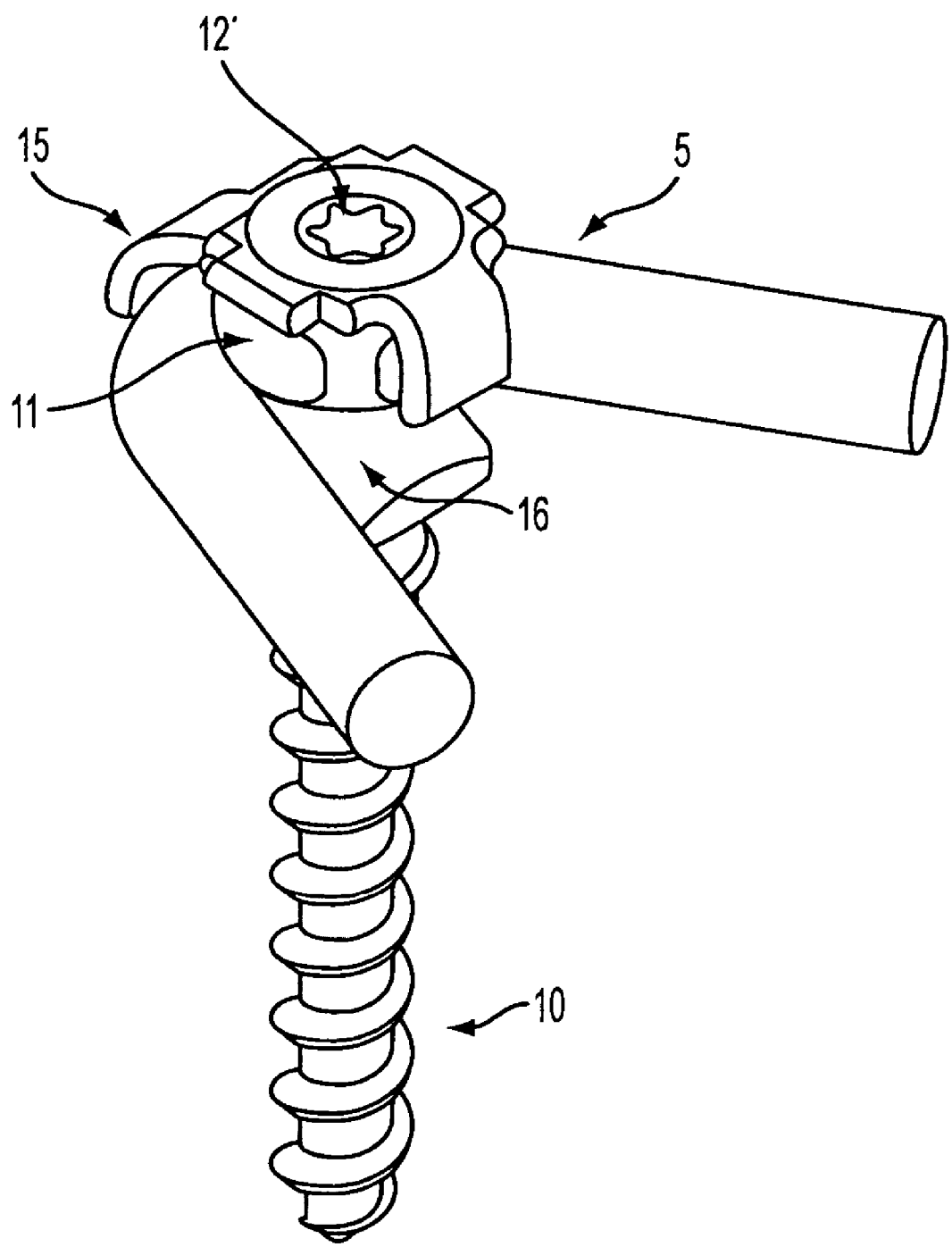
FIG. 12 illustrates an exemplary gliding interconnection between flexible interconnection means and vertebral anchoring means.

FIG. 3 illustrates an embodiment of the invention where at least three vertebrae (100,101,101') are implanted with anchoring means. In this representation the central anchoring means is positioned on the apical vertebra (100) (A) of the deformity on the posterior aspect of the vertebral body. The other elements of vertebral fixation above and below are implanted on the anterior portion of the vertebral bodies in such a manner as to create an angle ($\alpha$) between the anchoring means. The supple/flexible interconnection means preferably is attached to at least two bone anchoring means at the ends of the construct (vertebrae 101 and 101'). The attachment to the central vertebra (Vertebra 100) can be rigid with the interconnecting supple/flexible element (5), or it may be a gliding, or non-rigid connection. The advantage of a gliding interaction would be a more even distribution of forces across the entire construct while still permitting corrective forces across selected implants. FIG. 12 illustrates an exemplary gliding attachment of flexible interconnection means (5).

In terms of example of suitable anchoring means, bone fixation elements preferably are utilized. FIG. 10 illustrates a bone screw (1) as one suitable anchoring means. This screw preferably includes two distinct parts: (i) a bone threading (10) to permit anchorage in a vertebra; and (ii) a head (11). The head of the screw (11) may contain a passage (13) for the introduction of the supple/flexible interconnection means. The head also contains a threaded passage (12) into which is seated a blocking screw permitting a firm locking of the supple/flexible interconnection means to the screw head. The threading (14) is not a requirement in all of the embodiments described herein, but it facilitates insertion into a plate or staple-type device, as shown in FIGS. 6-9.

It should be understood that in this representation, as well as in all others (FIGS. 4,5 and 11), that the vertebrae that are to be implanted with anchoring means are adjacent to one another, but the invention applies equally to included surgical strategies in which the implanted vertebrae may not be adjacent to one another. For example, in one embodiment, only the vertebrae 100, 102 and 102' (FIG. 1) might be implanted with a suitable anchoring means.

Figure 4:
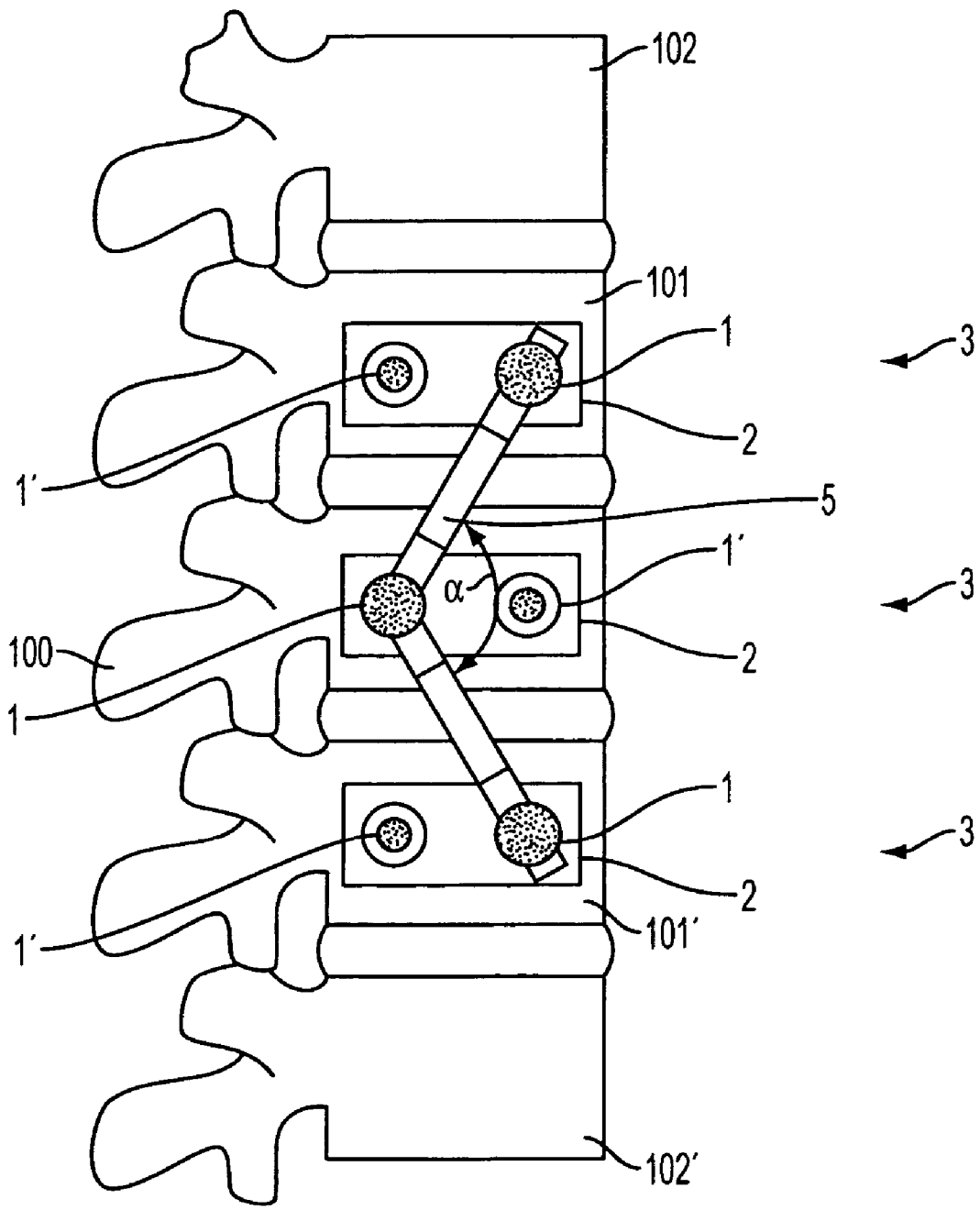
FIG. 4 illustrates another embodiment through an anterior application seen in a sagittal view of the spine.

FIG. 4 illustrates an additional embodiment whereby at least three vertebrae (100,101,101') receive two anchoring means each (1 and 1') in order to obtain an optimal bone anchorage. In this embodiment, the anchoring means may be linearly positioned on each vertebral body. In order to further augment the anchorage, the anchoring means (1 and 1') are connected to one another through a plate or staple like device (2).

Figure 9:
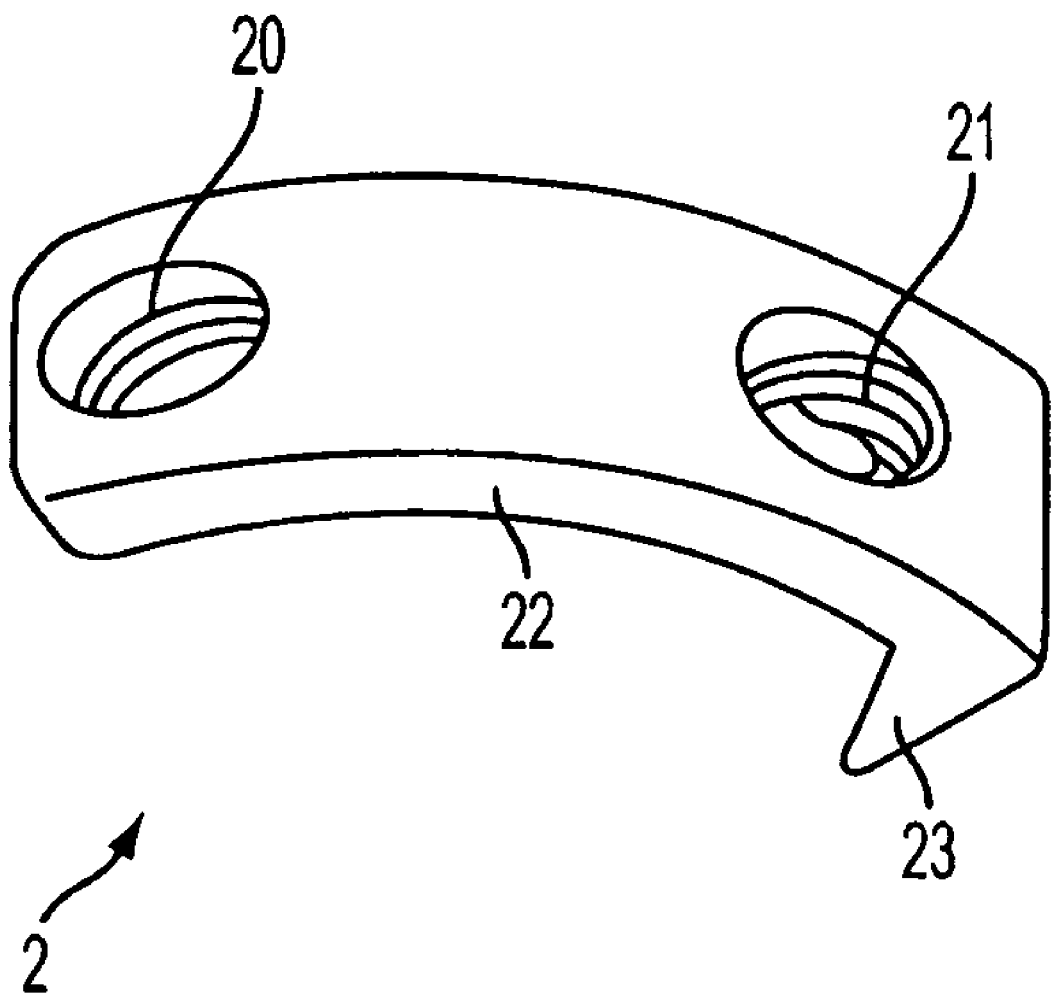
FIG. 9 illustrates a staple type device according to an embodiment, as depicted in elevated perspective.
Figure 10:
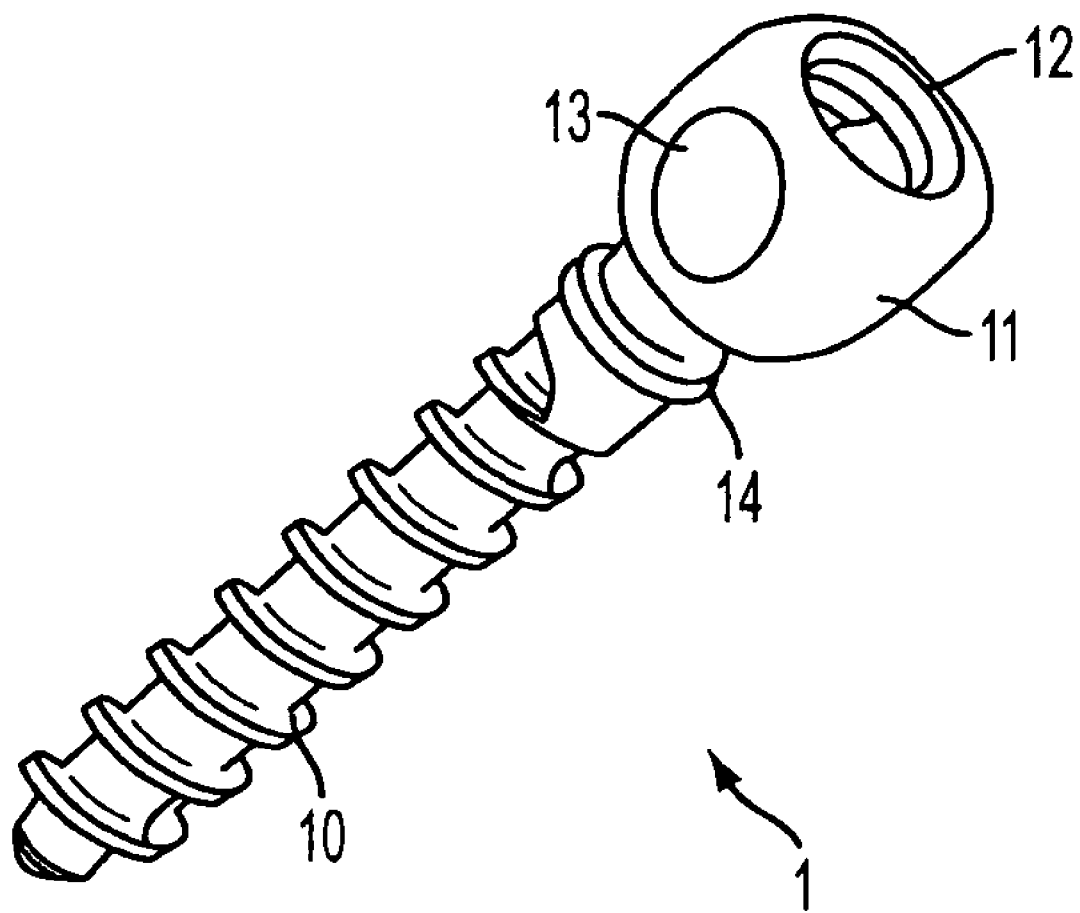
FIG. 10 illustrates a bone fixation element of a screw-type device according to an embodiment, as depicted in elevated perspective.

A preferred plate or staple-like device (2), is illustrated in more detail in FIG. 9. The device (2) preferably contains a radius of curvature (22) approximating the radius of curvature of a vertebral body. In order to assure proper seating and anchorage, the device (2), may include at least one spike (23). Two holes (20 and 21) are noted on the device (2) to permit seating of the anchoring means. For example, these holes (20 and 21) are threaded in order to fit with the threading of the anchoring means such as the bone screw illustrated in FIG. 10 (14 and 14' (not shown)).

Figure 8:
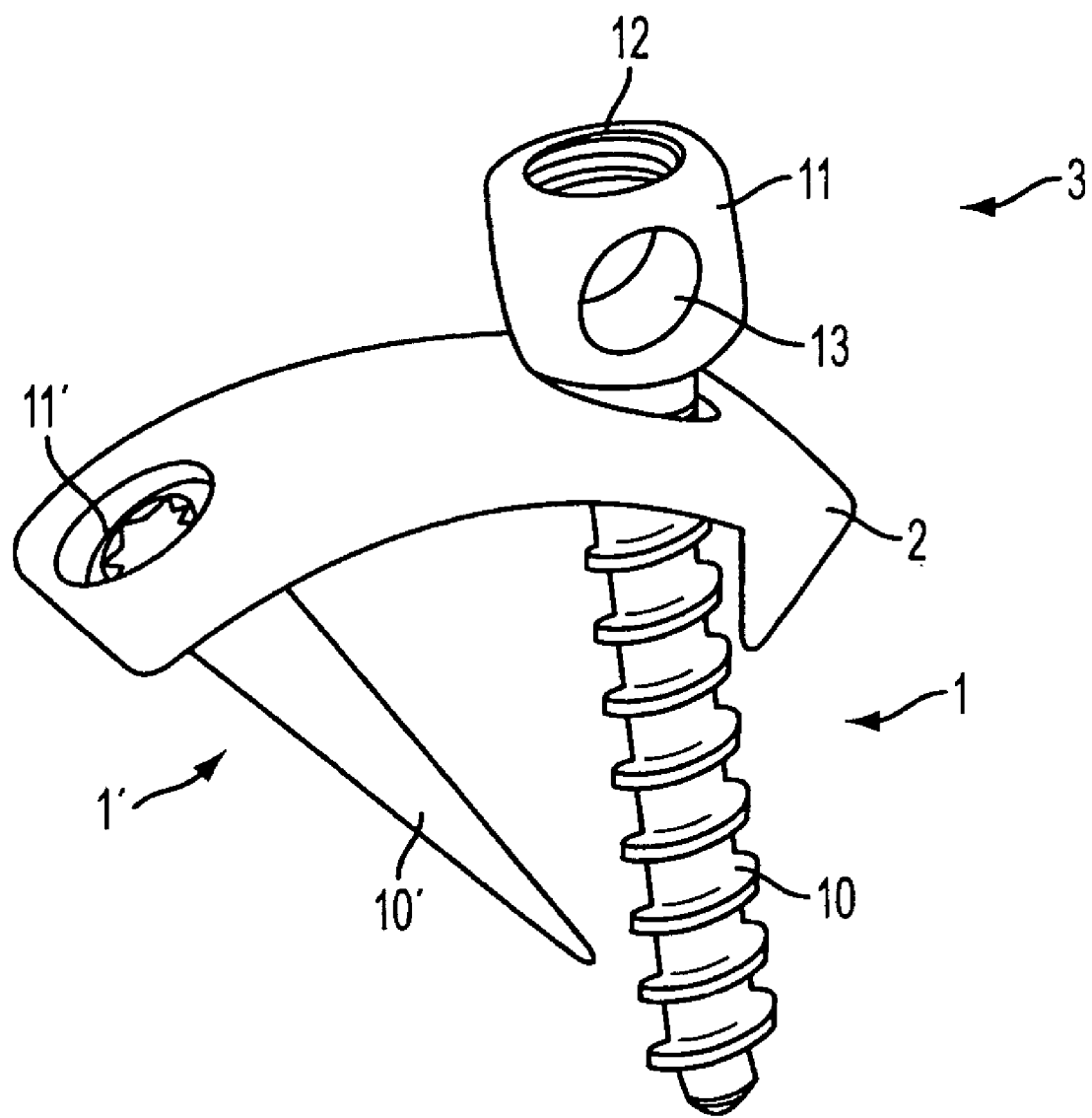
FIG. 8 illustrates a system of bone anchoring means according to additional embodiments seen in elevated perspective.

In a particularly preferred embodiment, anchorage to the vertebral body may occur through two types of anchoring means, as illustrated FIG. 8. The anchoring means (3) may include two 2 distinct elements: (i) a bone screw (1); and (ii) a nail (1'). The bone threading portion (10) of bone screw (1) permits solid anchorage into the vertebra, and comprises a threaded portion, and a head (11). The head (11) of the screw preferably contains a passage (13) for the introduction of the supple/flexible interconnection means. The head (11) also preferably contains a threaded passage (12) into which is seated a blocking screw (not shown) permitting a firm locking of the supple/flexible interconnection means (5) to the screw head. The threading of the neck of the screw, best seen in FIG. 10 (14), allows seating into the plate or staple-type device (2).

The other element of anchoring means (3), includes the nail (1'), which preferably includes a tip and shaft (10') for bone anchorage, and a head (11') containing a threading for fixation to the device (2). The tip and shaft (10') are illustrated here to be smooth, but those skilled in the art recognize that the tip and shaft (10') also could be fitted with a threading like a bone screw.

Figure 5:
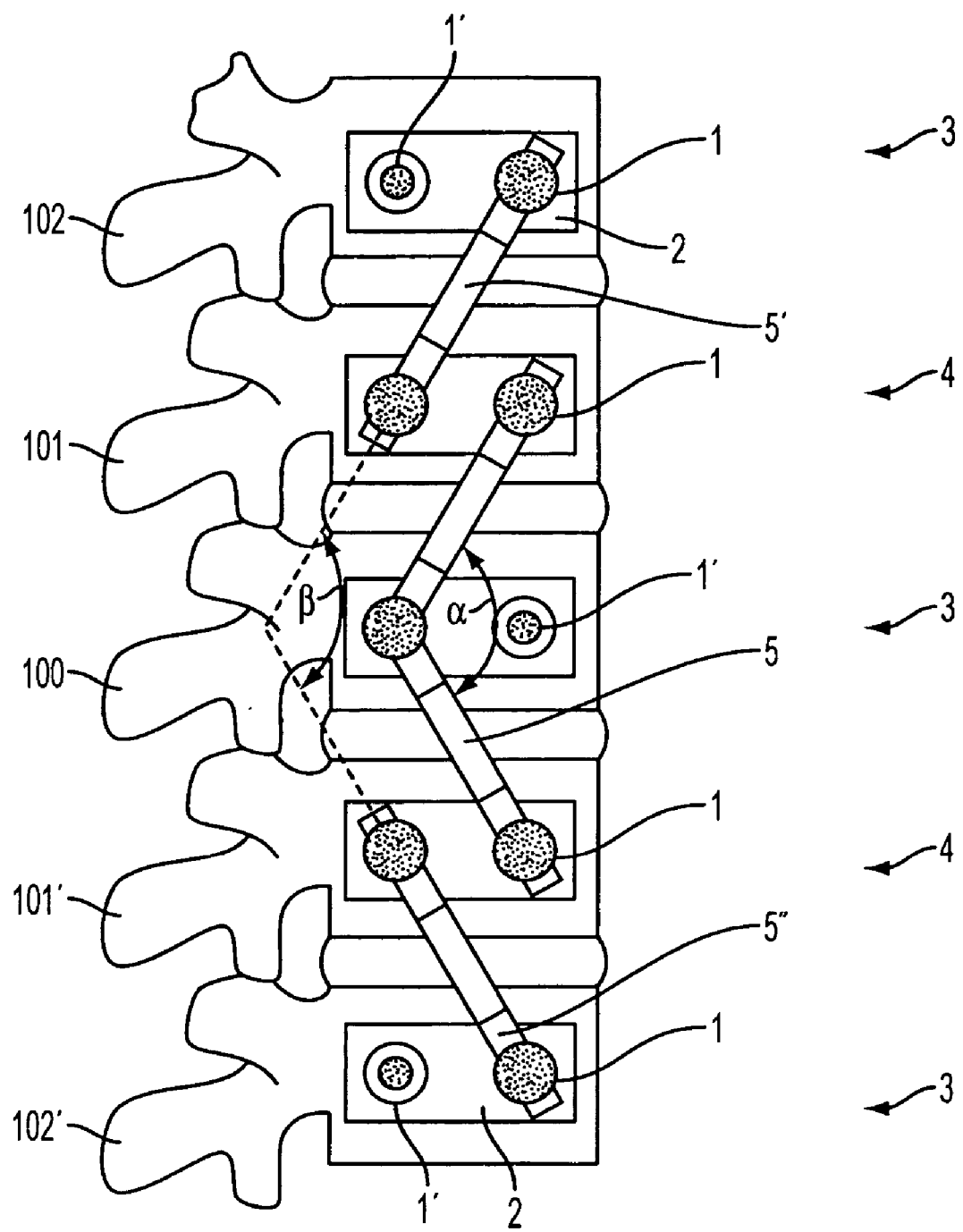
FIG. 5 illustrates an additional embodiment through an anterior application seen in a sagittal view of the spine.
Figure 6:
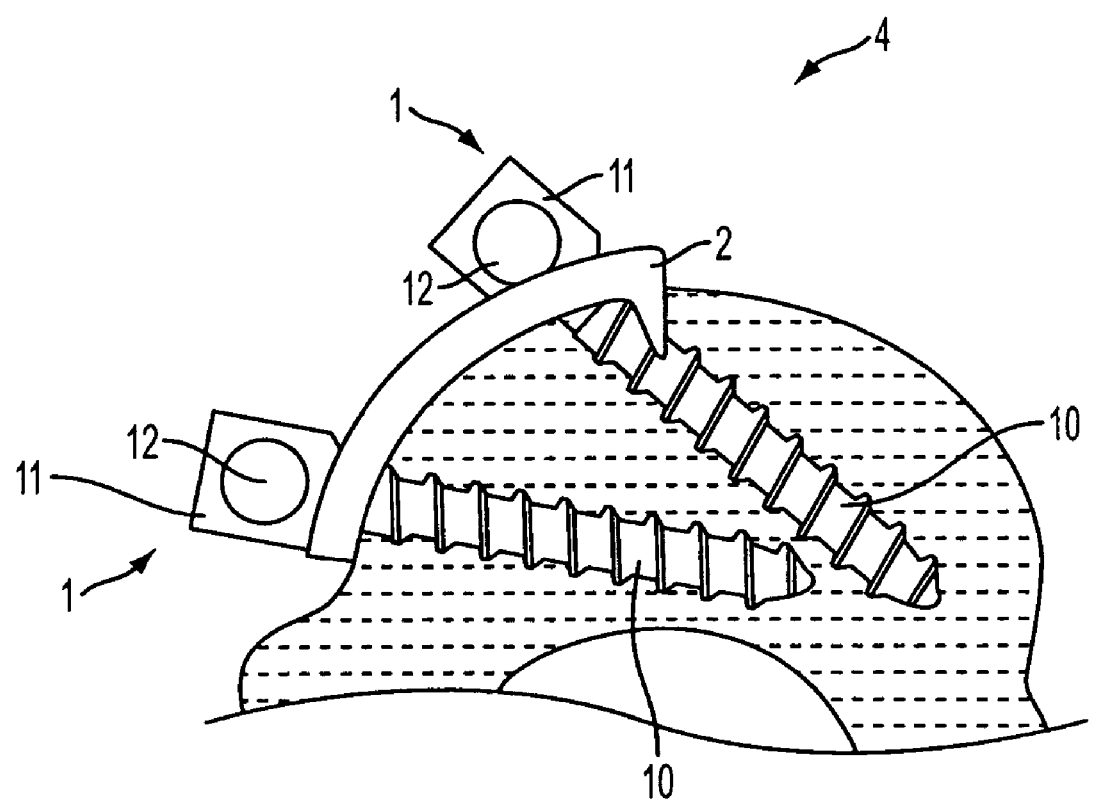
FIG. 6 illustrates a system of bone anchoring means according to an embodiment in cross sectional representation of a spinal vertebra.
Figure 7:
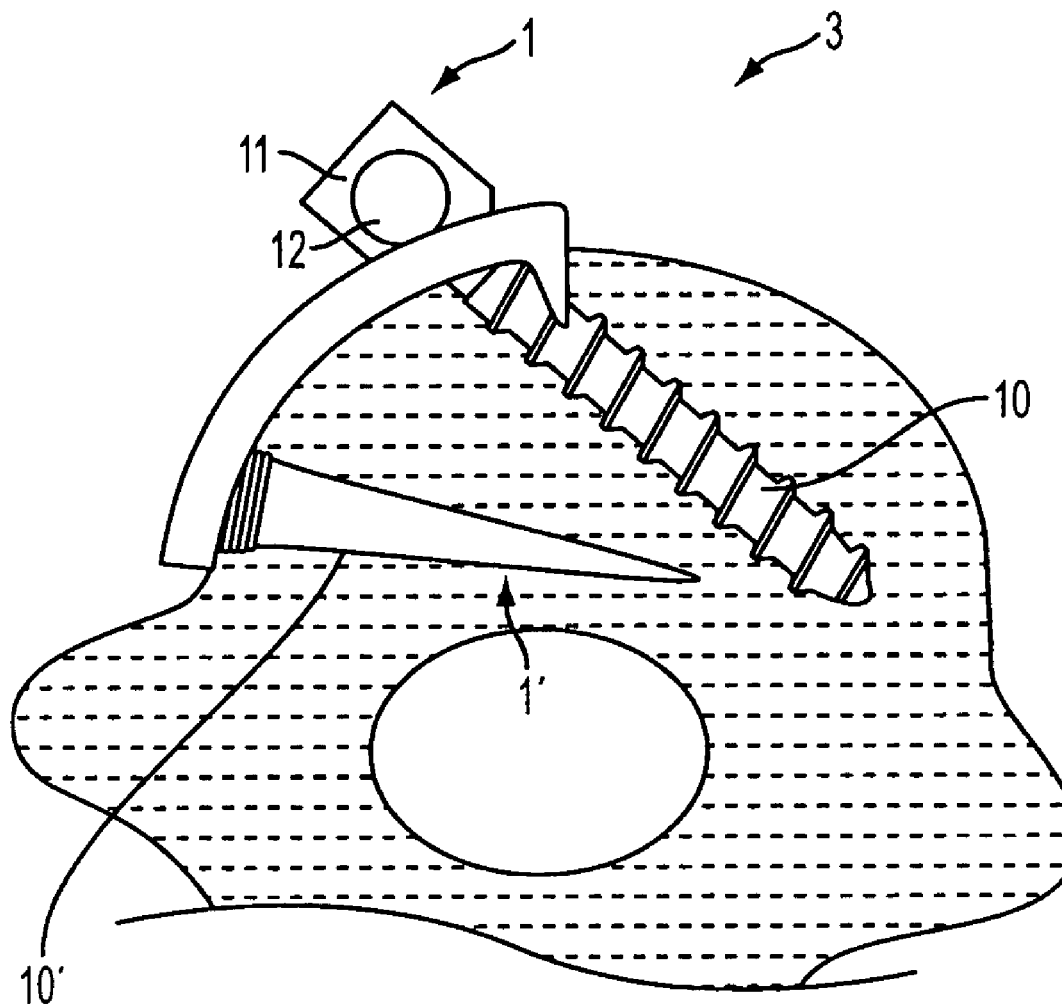
FIG. 7 illustrates a system of bone anchoring means according to another embodiment in cross sectional representation of a spinal vertebra.

The ensemble of anchoring means illustrated in FIGS. 4 and 5, i.e, two anchoring means per vertebra, also is illustrated in FIGS. 6 and 7. The anchoring means, or bone fixation elements (1 and 1') are interchangeable in their position on the device (2). The angle created by the two anchoring means (shown in FIGS. 6 and 7), avoids possible avulsion of the ensemble of bone fixation from the vertebra. In addition, the device (2) may include one bone screw (1) and one nail (1'), denoted by (3) in FIGS. 7 and 8, or the device (2) may include two bone screws (1 and 1), denoted by (4) in FIG. 6. The device (2) also could include any other anchoring means suitable for anchoring into a vertebral body. The guidance of anchoring means (1 and 1') via the holes in the device (2) assists in the proper implantation into a vertebra.

The anchoring means in the form of a bone screw (1) is placed on the posterior aspect of the vertebral body. This bone screw (1) contains passage (13) for placement of the flexible interconnection means (5) of the ensemble of elements on the central vertebra (100) at the apex of the spinal deformity (A).

As seen in FIG. 4, an anchoring means (1) containing a passage for placement of the interconnection means (5) of the ensemble of elements for bone fixation of the upper and lower vertebrae preferably is implanted on the vertebral body in such a manner as to create an angle ($\alpha$) between the elements of anchoring means across vertebral levels. As will be appreciated by the embodiment depicted in FIG. 4, the respective anchoring means in each respective vertebral body may be in a linear relationship with respect to one another, but the supple/flexible interconnection means (5) is attached to offsetting anchoring means (either rigid or gliding attachment) to provide a non-linear attachment having an angle of, for example, ($\alpha$). The supple/flexible interconnection means (5) preferably is attached to at least two anchoring means at the ends of the construct (vertebrae 101 and 101'). The attachment to the central vertebral anchoring means (vertebra 100) can be a solid/firm connection or a gliding interaction without fixation of the supple/flexible interconnection means (5). The advantage of a gliding interaction is believed to be a more desirable distribution of forces across the entire construct.

An additional embodiment is illustrated in FIG. 5. As show in FIG. 5, at least five vertebrae (100,101,101', 102,102') are instrumented with an ensemble of anchoring means and devices (2), shown either in configuration 3 (FIGS. 7 and 8), or configuration 4 (FIG. 6). This embodiment represents an extension of the embodiment described above. In order to create the configuration (4), two elements of the screw type fixation (1) are positioned in a plate or staple-like device (2), as shown in FIG. 6. This configuration 4 preferably is inserted between the configuration 3, shown in FIGS. 7 and 8, which preferably consists of one element of screw type bone fixation (1) and one nail type fixation (1') in a plate or staple-like device (2).

In this embodiment, the central vertebra (100), as well as the end vertebrae of the instrumented levels (102,102') remain instrumented in an identical fashion as described above, whereby the flexible interconnection means 5, 5', 5" is rigidly attached to the end anchoring means, and is glidably attached to the central anchoring means on vertebra (100). In addition, these vertebral bodies preferably are provided with a anchoring means in configuration 3. The method of fixation for the intermediate vertebrae of the construct preferably is configuration (4). This type of fixation is illustrated in FIG. 6 and preferably includes a plate or staple-like device (2), with two bone screws (1).

The advantage of the type of fixation shown as configuration 4 lies in the possibility of attaching 2 elements of supple/flexible interconnection means (5 and 5' or 5") to the same vertebra. The supple/flexible interconnection means (5) remains identical to that described for the second embodiment, creating an angle (α) across the implanted vertebrae. A second supple/flexible interconnection element (5', 5") preferably is applied for a connection to the intermediate and end anchoring means. The angle (β) created by the 2 interconnection elements (5', 5") at the ends of the construct, preferably is similar to the angle (α) of the central interconnecting element (5).

It is preferred that the angle (α) and/or (β) be within the range of from about 45 to about 145°, and preferably within the range of from about 65 to about 125°.

In accordance with the embodiments described herein, the angles (α) and/or (β) or just (α) as the case may be, represent the non-linear attachment of the interconnection means. As the skeletally immature spine matures and grows, or as deliberately exerted at the time of surgery (for mature or immature spines) the tension created on the anchor means and consequently, on the flexible interconnection means, is believed to cause these angles to increase. Thus, correction occurs by virtue of the flexible interconnection means being less non-linear (e.g., angles (α) and/or (β) have increased) after spinal growth and/or tensioning than they were prior to spinal growth or time of surgery (e.g., when implanted).

FIG. 12 illustrates an exemplary gliding interconnection between flexible interconnection means (5) and vertebral anchoring means (10). As shown the anchoring means (10) includes a head (11) and a threaded passage (12) into which is seated a blocking screw (12') permitting a firm locking of the supple/flexible interconnection means (5) to the screw head. The gliding connection is facilitated by use of a connecting passage (16), which in FIG. 12, is provided by the bottom portion of head (11) and an upper portion of a lower member positioned beneath head (11). Other connecting passages (16) are suitable for use in the invention, as will be appreciated by those skilled in the art. To prevent inadvertent slippage of flexible interconnection means (5), an additional hook member (15) may be provided, which in FIG. 12, is secured to head (11) via blocking screw (12').

While the invention has been described with reference to the preferred embodiment(s) thereof, it will be appreciated by those of ordinary skill in the art that various modifications can be made to the invention itself without departing from the spirit and scope thereof. All changes and modifications that are within the spirit of the invention are desired to be protected.

The invention claimed is:

1. A system for treating a spinal deformity in a skeletally mature or immature spine comprising:
   at least three vertebral anchor means for anchoring into three different vertebral bodies, two end vertebrae and at least one intermediate vertebral body respectively, wherein at least a first vertebral anchor means configured to be positioned on at least one end vertebrae, and at least a second vertebral anchor means configured to be positioned on at least one intermediate vertebral body are configured to be positioned non-linearly such that one of the at least first and the at least second vertebral anchor means is positioned closer to a posterior portion of a vertebral body, and the other of the at least first and the at least second vertebral anchor means is positioned closer to an anterior portion of an adjacent vertebral body, and wherein at least the first and at least a third vertebral anchor means each configured to be positioned on two end vertebrae includes a passage for the introduction of at least one flexible interconnection means, and a threaded passage for seating a blocking screw to secure flexible interconnection means by contact; and
   at least one flexible interconnection means attached to the at least three vertebral anchor means in a non-linear manner, wherein the flexible interconnection means are configured to constrain spinal growth, or permit deliberate intervertebral alignment changes by creating tension
   that causes a distraction of the at least first and at least third vertebral anchor means configured to be at the two end vertebrae, thereby causing a rotation of the at least one intermediate vertebrae due to interaction with the flexible interconnection means, and
   wherein the flexible interconnection means is attached through a gliding interconnection to the at least second vertebral anchor means for anchoring the at least one intermediate vertebral body, and the flexible interconnection means is rigidly attached to the at least first and the at least third vertebral anchor means for anchoring the two end vertebrae, the at least second vertebral anchor means comprising at least a head, a lower member positioned beneath the head, and a connecting passage provided by a bottom portion of the head and an upper portion of the lower member.

2. The system as claimed in claim 1, wherein the at least three vertebral anchor means are configured to be positioned in the vertebral bodies through an anterior approach to the spine.

3. The system as claimed in claim 1, wherein the system is configured to comprise one vertebral anchor means per vertebra.

4. The system as claimed in claim 1, wherein the at least three vertebral anchor means are configured to be applied on the convexity and involving the apex of the deformity.

5. The system as claimed in claim 1, wherein the at least three vertebral anchor means are configured to be implanted through a posterior approach to the spine and positioned with anchorage into the pedicles of selected vertebrae.

6. The system as claimed in claim 1, wherein the flexible interconnection means comprises a biocompatible ligament.

7. The system as claimed in claim 1, wherein the natural growth of the spinal column causes a distraction between the at least first and the at least third vertebral anchor means configured to be attached at the end vertebrae of the system.

8. The system as claimed in claim 1, wherein the tension causes a distraction of at least first and the at least third vertebral anchor means configured to be at the end vertebrae, or a tensioning of the interconnecting elements, resulting in a correction of spinal deformity in the frontal and sagittal planes.

9. The system as claimed in claim 1, wherein the system corrects spinal deformation in three dimensions, without fusion or rigid fixation of the affected vertebrae to one another.

10. The system as claimed in claim 1, wherein the at least second vertebral anchoring means further comprises a hook member to prevent inadvertent slippage of the flexible interconnection means.

11. A system for treating a spinal deformity in a skeletally mature or immature spine comprising:
at least three vertebral anchors for anchoring into three different vertebral bodies, two end vertebral bodies and at least one intermediate vertebral body respectively, wherein at least a first vertebral anchor configured to be positioned on at least one end vertebrae, and at least a second vertebral anchor configured to be positioned on at least one intermediate vertebral body are configured to be positioned non-linearly such that one of the at least first and the at least second vertebral anchors is positioned closer to a posterior portion of a vertebral body, and the other of the at least first and the at least second vertebral anchors is positioned closer to an anterior portion of an adjacent vertebral body; and
at least one flexible element attached to the at least three vertebral anchors in a non-linear manner,
wherein the flexible element is configured to constrain spinal growth, or permit deliberate intervertebral alignment changes, by creating tension
that causes the at least first and at least second vertebral anchors positioned non-linearly to be less non-linear after spinal growth than prior to spinal growth because the tension causes a distraction of the at least first and an at least third vertebral anchors positioned on the end vertebrae, thereby causing a rotation of the intermediate vertebrae due to interaction with the flexible element; and
wherein the flexible element is attached through a gliding interconnection to the at least second vertebral anchor for anchoring the at least one intermediate vertebral body, and the flexible element is rigidly attached to the at least first and the at least third vertebral anchors for anchoring the two end vertebral bodies, the at least second vertebral anchor comprising at least a head, a lower member positioned beneath the head, and a connecting passage provided by a bottom portion of the head and an upper portion of the lower member.

12. The system of claim 11, wherein the at least three vertebral anchors are configured to be positioned in the vertebral bodies through an anterior approach to the spine.

13. The system of claim 11, wherein the spinal deformity comprises a convexity and the at least three vertebral anchors are configured to be applied on the convexity and involving the apex of the deformity.

14. The system of claim 11, wherein the flexible element comprises a biocompatible ligament.

15. The system of claim 11, wherein the natural growth of the spinal column causes a distraction between the at least first and at least third vertebral anchors configured to be attached at the end vertebrae of the system.

16. The system of claim 11, configured so that tension of the flexible element will be caused by spinal growth, thereby causing a correction of spinal deformity in the frontal and sagittal planes.

17. The system of claim 11, wherein the system corrects spinal deformation in three dimensions, without fusion or rigid fixation of the affected vertebrae to one another.

18. The system as claimed in claim 11, wherein the at least second vertebral anchor further comprises a hook member to prevent inadvertent slippage of the flexible element.

* * * * *